United States Patent [19]

Mina

[11] Patent Number: 4,754,077

[45] Date of Patent: Jun. 28, 1988

[54] ANTIOXIDANT SYNTHESIS

[75] Inventor: George L. Mina, Orangeburg, S.C.

[73] Assignee: Ethyl Corporation, Richmond, Va.

[21] Appl. No.: 846,085

[22] Filed: Mar. 31, 1986

Related U.S. Application Data

[63] Continuation-in-part of Ser. No. 450,207, Dec. 16, 1982, abandoned.

[51] Int. Cl.$^4$ .............................................. C07C 45/00
[52] U.S. Cl. ...................................... 568/662; 568/720
[58] Field of Search ................................ 568/662, 770

[56] References Cited

U.S. PATENT DOCUMENTS

| | | | |
|---|---|---|---|
| 2,838,571 | 6/1958 | Filbey | 568/662 |
| 2,841,623 | 7/1958 | Norton et al. | 568/662 X |
| 2,841,624 | 7/1958 | Norton et al. | 568/662 X |
| 2,962,531 | 11/1960 | Coffield | 568/660 |

FOREIGN PATENT DOCUMENTS 1327542  8/1973  United Kingdom .

OTHER PUBLICATIONS

Kako, Chem. Abs., vol. 96, (1982) 19815 y.

Primary Examiner—James H. Reamer
Attorney, Agent, or Firm—John F. Sieberth; J. D. Odenweller

[57] ABSTRACT

A process for making a 2,6-di-hydrocarbyl-4-alkoxyalkylphenol, e.g. 2,6-di-tert-butyl-4-methoxymethylphenol, by reacting a 2,6-dihydrocarbylphenol with formaldehyde in a stoichiometric excess of alcohol and in the presence of a Mannich base catalyst preferably formed in situ by adding a catalyst-forming amount of a secondary amine, e.g. dimethylamine, to the mixture of 2,6-di-hydrocarbylphenol, formaldehyde and alcohol. Unreacted alcohol and amine are distilled out and the 2,6-di-hydrocarbyl-4-alkoxyalkylphenol is reacted with a benzene-type compound, e.g. mesitylene, to make a hindered phenolic antioxidant, e.g. 1,3,5-trimethyl-2,4,6-tri-(3,5-di-tert-butyl-4-hydroxybenzyl)benzene.

19 Claims, No Drawings

ANTIOXIDANT SYNTHESIS

This application is a continuation-in-part of copending application Ser. No. 450,207 filed Dec. 16, 1982 now abandoned.

BACKGROUND OF THE INVENTION

I. Field of the Invention

This invention relates in general to processes for forming high molecular weight hindered phenols and intermediates therefor. This invention relates in particular to an improved catalyst/solvent system for the formation of hindered phenols.

II. Description of the Prior Art

The hindered phenols ultimately formed by the process of this invention and earlier processes have been widely used as antioxidants in food, packaging materials, stock chemicals, plastics and the like. A process to produce such hindered phenols is set forth in Rocklin et al., U.S. Pat. No. 3,026,264 which is incorporated herein by reference in its entirety. An improvement on the Rocklin et al. process is disclosed in my U.S. Pat. No. 4,340,767 which is also incorporated herein by reference in its entirety.

There exists a need to reduce the processing and materials cost used in the production of antioxidants such as 1,3,5-trimethly-2,4,6-tris(3,5,-di-tert-butyl-4-hydroxybenzl)benzene. The prior art processes have used, for example, 3,5-dialkyl-4-hydroxybenzly alcohol (also called 2,6-dialkyl-α-hydroxy-p-cresol) as an intermediate to produce the high molecular weight hindered phenols. The alcohol intermediates must be isolated from their reaction mass as a solid by means of centrifugation which is quite expensive. Also, adequate washing of the solid filter cake has proven difficult and some of the wash solvents may be carried forward into the product causing various problems.

The 3,5-di-tert-butyl-4-hydroxybenzyl alcohol is often used as an intermediate. However, this intermediate is insoluble in preferred solvents such as methylene chloride. Thus strict stoichiometry controls are required and undesirable side reactions with sulfuric acid catalyst may occur. Finally, the use of an alcohol intermediate produces significant amounts of "heel" and certain bisphenols which, while usable, tie the subject process to other processes and markets.

The substitution of alkyl ethers of intermediate alcohols has been suggested to produce high molecular weight hindered phenols. However, the ethers are not always available and their production has not been cost effective.

SUMMARY OF THE INVENTION

The present invention is directed to the reduction of costs in the production of high molecular weight hindered phenols, commonly used as antioxidants. The present invention is a process for the production of aromatic ethers of structure I:

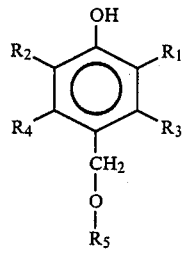

comprising reacting at a temperature of 50°–200° C. in the presence of a Mannich base catalyst: formaldehyde; a stoichiometric excess of an alcohol of structure II:

where $R_5$ is alkyl or cycloalkyl; and a substituted phenol of structure (III):

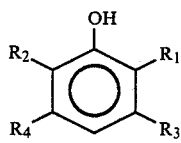

wherein $R_1$ and $R_2$ are the same or different and are selected from alkyls, cycloalkyls, aryls, aralkyls and alkaryls; and $R_3$ and $R_4$ are the same or different and are selected from H, alkyls, cycloalkyls, aryls, alkaryls aralkyls.

The present invention is also a process for the production of high molecular weight hindered phenols, said process comprising the steps of:

(a) reacting at a temperature of 50°–200° C. in the presence of a Mannich base catalyst
 (i) formaldehyde,
 (ii) a stoichiometric excess of an alcohol of structure (II):

wherein $R_5$ is alkyl or cycloalkyl, and
 (iii) a substituted phenol of structure (III):

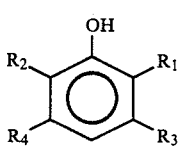

wherein $R_1$ and $R_2$ are the same or different and are selected from alkyls, cycloalkyls, aryls, aralkyls and alkaryls; and $R_3$ and $R_4$ are the same of different and are selected from H, alkyls, cycloalkyls, aryls, aralkyls and alkaryls so as to form an aromatic ether of structure (I):

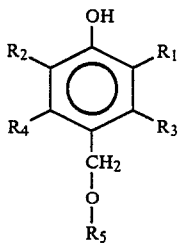

(b) removing the excess unreacted alcohol;

(c) adding a hydrocarbon or halogenated hydocarbon solvent; and (d) reacting the aromatic ether of structure (I) with benzene or an alkylated benzene.

The present invention is also a process for the production of 1,3,5-trimethyl-2,4,6,-tris(3,5,-di-tert-butyl-4-hydroxybenzyl)benzene with conservation of catalyst materials, elimination of centrifugation of a chemical intermediate, and minimization of by-product bisphenol intermediate, said process comprising the steps of:

(a) reacting 2,6,-di-tert-butylphenol, formaldehyde, and a stoichiometric excess of methanol in the presence of a catalytic portion of 2,6-di-tert-butyl-4-dialkylaminomethylphenol so as to form the intermediate 2,6-di-tert-butyl-α-methoxy-p-cresol, said catalytic portion being formed from a dialkyl secondary amine, whereby some of the secondary amine remains in the unreacted excess methanol and formation of 4,4'-methylenebis(2,6-di-tert-butylphenol) is minimized;

(b) recovering the unreacted excess methanol containing some of the secondary amine and recycling said methanol to another intermediate formation reaction thereby conserving catalyst;

(c) dissolving the intermediate 2,6-di-tert-butyl-α-methoxy-p-cresol in methylene chloride thereby eliminating the need for centrifugation;

(d) reacting the dissolved intermediate with mesitylene in the presence of a sulfuric acid or Friedel-Crafts catalyst; and (e) recovering the 1,3,5-trimethyl-2,4,6-tris(3,5-di-tert-butyl-4-hydroxybenzyl)benzene product.

It is therefore an object of the present invention to provide an improved process for the economic production of phenolics from alkyl ethers of certain alcohols.

It is also an object of the present invention to provide an improved catalyzed process for the production of alkyl ethers from hindered phenols.

It is also an object of the present invention to eliminate expensive product recovery equipment/techniques and to minimize by-product formation in the production of hindered phenols.

These and other objects, advantages, and applications of the present invention will become apparent to those skilled in the art by a reading of the following description of examples of the best mode contemplated for practicing the invention.

DESCRIPTION OF THE PREFERRED EMBODIMENT

The present invention has been demonstrated as a clean process for the production of certain ethers of hindered paracresols as intermediate compounds. The invention is also a process to produce high molecular weight hindered phenols formed from the intermediate aromatic ethers and benzene compound to be combined therewith.

The aromatic ether compounds of the invention are of the general structure I:

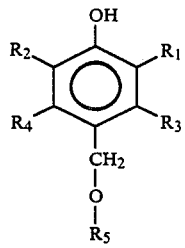

where $R_1$ and $R_2$ are the same or different and are selected from straight chain or (preferably) branched alkyls, cycloalkyls, aryls, aralkyls and alkaryls; $R_3$ and $R_4$ are the same or different and are selected from H (preferably), alkyls, cycloalkyls, aryls, alkaryls and aralkyls; and $R_5$ is alkyl, preferably of 1 to 6 carbon atoms, or cycloalkyl of 5-12 carbon atoms.

The alcohols of the invention are of the general structure II:

$$R_5\text{—OH} \qquad (II)$$

where $R_5$ is as defined above. These alcohols include methanol, isopropanol, ethanol, sec-butanol, n-hexanol, cyclopentanol, isoamyl alcohol, n-propanol, n-butanol, and others. Preferred alcohols are the lower alkyl alcohols such as methanol, isopropanol, sec-butanol, and n-hexanol. More preferred are the unbranched lower alkyl alcohols. These include methanol, n-butanol, ethanol, n-hexanol and the like. Most preferred are the $C_1$–$C_4$ straight chain alkyl alcohols. Most especially preferred is methanol since methanol reacts quickly and completely in the inventive process, is readily available, and carries catalyst over into the recycled excess methanol when used as a solvent/reactant.

The cycloalkyls and branched alkyl groups are preferred substituents for $R_1$ and $R_2$. Branched alklys and cycloalkyls of 1 to 6 carbons are more preferred and the tert-butyl group is the most preferred substituent for $R_1$ and $R_2$ because of its strong hindrance effect for phenols, especially where an antioxidant use is proposed.

The substituted phenols of the invention have the general structure III:

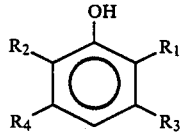

wherein $R_1$, $R_2$, $R_3$ and $R_4$ are as defined above. Examples of the phenols suitable to make the aromatic ether of the invention include:
2,6-di-tert-butylphenol;
2,6-diisopropylphenol;
2,6-sec-butylphenol;
2-methyl-6-tert-butylphenol;
2,6-diethylphenol;
2,6-dicyclopentylphenol;
2,6-dicyclohexylphenol;
2-cyclopentyl-6-tert-butylphenol;

2,6-diisopropyl-3-methylphenol;
2,6-di-tert-butyl-3,5-dimethylphenol;
2,3,6-triisopropylphenol;
2,3,6-triethylphenol;
and the like. More preferred are the 2,6-di-lower alkylphenols and 2,6di-lower cycloalkyphenols, otherwise unsubstituted, i.e., where $R_3$ and $R_4$ are both H. These include:
2,6-di-tert-butylphenol;
2,6-dimethylphenol;
2,6-dicyclopentyphenol;
2,6-diisopropylphenol;
2-methyl-6-tert-butylphenol;
2-ethyl-6-sec-butylphenol;
and the like.

Most preferred are those, 2,6-di-lower-alkylphenols otherwise unsubstituted where the lower alkyl substituents are identical such as 2,6diisopropylphenol, 2,6-di-sec-butylphenol, and 2,6-di-tert-butylphenol. Most highly preferred is the compound 2,6-di-tert-butylphenol.

The intermediate ethers of the invention include but are not limited to:
2,6-di-tert-butyl-α- methoxy-p-cresol;
2,6-di-tert-butyl-α- ethoxy-p-cresol;
2,6-di-tert-butyl-3,5,-dimethyl-α-methoxy-p-cresol;
2,6-dicylclopentyl-α-methoxy-p-cresol;
2,6-di-tert-amyl-α-butoxy-p-cresol;
2,6-di-sec-butyl-α-cyclohexoxy-p-cresol;
2,6-dicyclohexyl-αmethoxy-p-cresol;
2,6-dimethyl-α-propoxy-p-cresol;
2-methyl-6-tert-butyl-α-methoxy-p-cresol;
2-ethyl-6-octadecyl-α-ethoxy-p-cresol;
2-methyl-6-cyclooctyl-α-methoxy-p-cresol;
2-(α,α-dimethylbenzyl)-6-methyl-α-methoxy-p-cresol;
2-methyl-6-isopropyl-α-cyclopentoxy-p-cresol;
and others.

Most secondary amines are acceptable for the process. The preferred amines have the structure IV:

(IV)

wherein $R_6$ and $R_7$ are separately the same or different and are selected from alkyl, cycloalkyl, alkanol, cycloalkanol, aromatic, heterocyclic or together with the nitrogen to which tey are attached form a ring.

Representative examples of these amines are dimethylamine, diethylamine, methylethylamine, diisoamylamine, dibenzylamine, methylisobutylamine, diisobutylamine, dicyclohexylamine, methylcyclohexylamine, ethylcyclopentylamine, methylcyclooctylamine, diethanolamine, methylethanolamine, methyl(2-hydroxybutyl)amine, methyl(2-hydroxycyclohexyl)amine, ethyl(4-hydroxycyclohexyl)amine, N-methylaniline, methyl-o-tolylamine, dibenzylamine, methylbenzylamine, methyl(α-methylbenzyl)amine, N-(3-methylaminopropl)morpholine, piperidine, piperazine, morpholine, and the like.

The dialkylamines, dicycloalkylamines and alkanolamines are most preferred since they are readily available, cheap, and selectively form Mannich base compounds. While long chain alkylamines are usable, their use amy required selection of an expensive solvent/reactant to form the ether intermediate. Included among the more preferred amines are dimethylamine, diethylamine, dipropylamine, di-n-butylamine, diisoamylamine, methylethylamine, diisopropylamine, didodecylamine, methylisopropylamine, and the like. Still more preferably $R_6$ and $R_7$ are lower alkyl groups containing 1 to 4 carbon atoms such as dimethylamine, diethylamine, methylethylamine, diisopropylamine, methylisobutylamine and the like. The most preferred dialkylamines are dimethylamine and diethylamine, especailly dimethylamine.

Preferred alkanolamines are those in which the alkanol groups contain about 2 to 4 carbon atoms such as diethanolamine, methylethanolamine, di-(2-hydroxypropyl)amine, di-(2-hydroxybutyl)amine, ethylethanolamine, isobutylethanolamine and the like. The most preferred alkanol amines are the dialkanolamines especially diethanolamine. Also suitable is methyl-N,N'-diethylethylenediamine. Other usable secondary amines include piperidine, 1,2,3,4,-tetrahydroisoquinoline, 6-methoxy-1,2,3,4,-tetrahydroisoquinoline, morpholine, piperazine, ω-methylaminopropiophenone, β-acetylethylbenzylamine, benzyl-(2-cyclohexanonylmethyl)amine, and 3,4,-methylenedioxybenzyl-(2-cyclohexanonylmethyl)amine.

Dimethylamine is the most preferred of all secondary organic amines because it readily forms catalyst in the preferred solvent, methanol. Mixtures of secondary amines may be used.

The invention uses a Mannich base catalyst to produce the alkyl ethers of para-cresols. The Mannich base catalyst is readily formed by the addition of a secondary organic amine to a combination of formaldehyde and a hindered phenol such as 2,6-di-tert-butylphenol or 2,6,-di-cyclopentylphenol.

The catalyst of the invention may be formed in situ with formaldehyde and the substituted phenol by addition of a suitable secondary amine to form a structure (V):

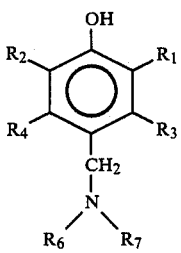

(V)

where $R_1$, $R_2$, $R_3$, $R_4$, $R_6$ and $R_7$ are as defined above. Such Mannich base compounds can also be used in the process of the invention by their simple addition to the (substituted) benzene and a compound of structure (I), with appropriate catalyst at suitable reaction conditions.

Examples of Mannich base compounds of structure (V) are:
2,6-di-tert-butyl-4-dimethylaminomethylphenol;
2,6-diisopropyl-4-dimethylaminomethylphenol;
2,6-di-tert-butyl-4-diethylaminomethylphenol;
2-methyl-6-tert-butyl-4-dimethylaminomethylphenol;
2,6-diethyl-4-diethanolaminomethylphenol;
and the like.

The high molecular weight hindered phenols according to the invention include those formed from the above ethers and a benzene or alkylated benzene. The methyl substituted benzenes such as toluene, xylene isomers, trimethylbenzene isomers, and durene are preferred. Mesitylene(1,3,5,-trimethylbenzene) is most preferred since it may be used to form the valuable antioxidant 1,3,5-trimethyl-2,4,6-tris(3,5,-di-tert-butyl-4-hydroxybenzyl)benzene and similar homologs. Other suitable compounds include 1,3,5-triethylbenzene, 1,4-diisopropylbenzene, 1,3,-dimethyl-5-ethylbenzene, 1,2,4,5-tetramethylbenzene, 1,2,-dimethyl-4,5-diethylbenzene, 1-n-butyl-3-ethyl-5-methylbenzene and the like.

Preferably, a small amount, e.g. 0.01–0.1 mole per mole of substituted phenol, of dimethlamine is added to a 2,6-dialkylphenol, formaldehyde (flake or para-formaldehyde) and methanol (sufficiently in excess to act as solvent) in situ. Heating promotes catalyst formation, thus the amine may merely be added at the start of the reaction sequence so as to form the catalyst for reaction. The preferred catalysts are the 2,6-dialkyl-α-dimethylamino-p-cresols. The compound 2,6-di-tert-butyl-α-dimethylamino-p-cresol is most preferred.

When a 2,6-dialkylphenol is used as the limiting reactant, dimethylamine remains dissolved in the excess methanol or other reactant/solvent and is thus carried over for reuse in subsequent reactions.

Both sulfuric acid and Friedel-Crafts catalysts are suitable according to the invention for formation of high molecular weight hindered phenolic compounds. Sulfuric acid is preferred but suitable Friedel-Crafts catalysts include $AlCl_3$, $AlBr_3$, $FeCl_3$ and the like.

Suitable solvents for reaction of a benzene or alkylbenzene with the alkyl ethers of the invention include various hydrocarbons and, preferably, halogenated hydrocarbons. These include the paraffins, especially $C_5$–$C_{10}$ compounds such as pentane, isopentane, hexane, cyclohexane, heptane, octane, isooctane, and decane as well as mixture of these. Also included are alkane halides such as 1,1-dichloropropane, 1,2-dichloropropane, 2,2-dichloropropane, 1,1-dichloroethane, 1,2-dichloroethane, 1,1,1-trichloroethane, n-butylchloride, sec-butylchloride, isobutylchloride, chloroform, carbon tetrachloride and the like. Methylene chloride is the especially preferred solvent for production of the high molecular weight hindered phenols.

The amount of solvent may vary so long as dissolution of the ingredients is achieved to the extent required for reaction. A useful range is 50–500 parts solvent per 100 parts reactant phenol. A preferred range is from 100–200 parts solvent per 100 parts reactant.

The compounds made by this invention have proven antioxidant activity and are, therefore, very useful.

The present invention is especially advantageous over prior art processes not only because of its one pot procedure but also because it minimizes the production of bisphenol coproducts, notably 4,4'-methylenebis(2,6-di-tert-butylphenol).

Earlier attempts to prepare the chemical intermediate of the invention used a strong base catalyst such as potassium hydroxide (KOH). This resulted in the conversion of 25 percent or more of the starting hindered phenol to a bisphenol. While the bisphenol is a usable compound, it is not nearly as valuable as the chemical intermediate of the invention. Furthermore, such prior art processes unnecessarily tied the production of high molecular weight hindered phenols to a relatively lower weight phenolic. When the inventive process is operated with 2,6-di-tert-butylphenol, the conversion to 4,4'-methylenebis(2,6-di-tert-butylphenol) is as low as five percent or less with nearly complete conversion to the desired chemical intermediate.

According to the invention, the formaldehyde, hindered phenol, excess lower alcohol, and small amount of catalyst are heated to an elevated temperature in a sealed reaction chamber thereby raising the pressure. A suitable reaction temperature range is 50°–200° C., preferably 60°–130° C. A suitable range of reaction presuure is 0–1,000 psig, preferably 5–100 psig. More preferably the reaction is carried out with methanol at about 60°–100° C. and 5–25 psig. Such conditions tend to limit the formation of compounds of the type 4,4'-methylene-bis-(2,6-dialkylphenol).

The procedure of the preferred embodiment permits a one pot process whereby excess solvent from formation of the alkyl ether of the phenol reactant is stripped off, the appropriate solvent for reaction with, e.g. mesitylene is added, and the high molecular weight hindered phenol is formed in situ. This obviates such as by centrifuge.

The preparation of phenolic compounds by the inventive process may be carried out in several fashions and the ingredients may be combined in any order prior to reaction. Preferably, the acid catalyst is added last. Multiple additions of catalyst may be made.

The ratio of reactants for preparation of the phenolic may be combined over a broad range, but excess solvent is preferred for better reaction mixing.

A slight excess of the structure (I) ether over stoichiometric is preferable since excess benzene or alkylated benzene may otherwise lead to an undesirable mixture of monosubstituted and polysubstituted benzenes.

The preparation of phenolic may be carried out over a broad range of temperatures but −60° to 140° C. is a usable range. About −10° C. to 30° C. is a preferred range and about 0° to 10° C. is more preferred.

Although superatmospheric and subatmospheric pressures may be used, they are unnecessary or uneconomical where a sufficiently active catalyst is used.

The following example serves to illustrate the best mode of the invention now known to me.

EXAMPLE 1

Preparation of Ether

To a 500 mL, 4-neck, round bottom flask equipped with mechanical stirrer, nitrogen inlet, reflux condenser, and side arm dropping funnel was charged the following:

220 mL methanol;
24.0 grams para-formaldehyde;
3.0 grams 40% dimethylamine in water.

The mixture was heated to reflux (about 68° C.) and a solution of 103.2 grams 2,6-di-tert-butylphenol in 50 mL methanol was added dropwise over a period of three hours under nitrogen flush and at reflux. The reaction mixture was transferred to a one-liter Parr pressure reactor equipped with dual pitch blade impellers. The reactor was heated to and maintained at 80° C. with stirring for four hours, whereupon the pressure in the reactor reached about 15–20 psig. The reaction mixture was cooled to about 65° C. and transferred to a one-liter Morton, creased, three-neck, round bottom flask equipped with a mechanical stirrer having a three-inch, half moon impeller, a thermometer, and a side dropping funnel distillation head. The reaction mixture was heated in the flask in a 100°–120° C. oil bath under nittogen flush with agitation to strip off solvent. When the reaction mass temperature reached 95° C. the oil bath was removed and an ice bath applied. Analysis confirmed formation of 2,6-di-tert-butyl-α-methoxy-p-cresol.

Preparation of Phenolic

The cooled Morton flask was set up for reflux and the following were added to the reaction mixture:
200 mL methylene chloride;
14.8 grams mesitylene; and
1.5 mL acetic acid.

The flask was cooled to 5° C. in an ice bath and stirred at 150 rpm. While maintaining the reaction mixture at 3°–7° C., about 25 ml 84% aqueous $H_2SO_4$ was added dropwise over two hours. The reaction mass was transferred to a separatory funnel and allowed to settle for about 15 minutes. The lower, acid phase was cut off and the remainder of the reaction mass was returned to the one-liter Morton flask. A second portion of 1.5 mL acetic acid was charged and a second 25 mL portion of 84% $H_2SO_4$ was added dropwise over two hours as above. The same procedure was followed to separate the acid phase. Thereupon the remaining reaction mass was charged to a one-liter resin flask equipped with four neck top, bottom stopcock, mechanical agitator, thermometer, nitrogen flush, and distillation/reflux head. To the reaction mixture is then added 360 mL deionized water and 100 grams soda ash. The reaction mixture was heated by means of the steam jacket to strip off methylene chloride until no more comes off overhead with a pot temperature of at least 85° C. The flask was set up for reflux and 800 mL heptane added. The reaction mass was heated to reflux and all solids dissolved whereupon the mass was allowed to settle for about five minutes before cutting off the lower aqueous phase. The reaction mass was washed twice with two 200 mL portions of deionized water and a pH of about 5-7 was determined. The hot heptane solution was transferred to a one liter, three-neck round bottom flask equipped with mechanical stirrer, thermometer, and nitrogen flask. The solution was cooled slowly to 5° C. and the resultant slurry was filtered on a Buchner funnel. The product was washed with 140 mL heptane and dried to provide 83.25 grams 1,3,5-trimethyl-2,4,6-tris(3,5-di-tert-butyl-r-hdyroxybenzyl)benzene of over 99 percent purity by high pressure liquid chromatography analysis.

COMPARATIVE EXAMPLES

As mentioned earlier, prior art processes for making the ether intermediate use alkali metal or alkaline earth metal hydroxide as the catalyst (Filbey, U.S. Pat. No. 2,838,571; Norton et al., U.S. Pat. No. 2,841,624). By way of comparison, an experiment was conducted to make the ether intermediate following the process of this invention and another experiment was conducted under identical conditions but replacing the secondary amine with NaOH as used by Norton et al. These experiments are described in the following two examples.

EXAMPLE 2

Process of Present Invention

In a reaction vessel under $N_2$ was placed 5.4 grams para-formaldehyde, 66 mL of methanol and 1.35 grams 40 weight percent aqueous dimethylamine (0.012 moles). This was heated to reflux and a solution of 30.9 grams (0.15 moles) of 2,6-di-tert-butylphenol in 15 mL methanol was added over a two hour period at reflux. The reaction mixture was then transferred under $N_2$ to a pressure reaction vessel. The vessel was sealed and heated at 95° C. for 2.5 hours with stirring. The solvent and volatiles were evaporated and the residue (37 grams) analyzed by gas chromatography. (See Table I)

EXAMPLE 3

Prior Art Process

In a reaction vessel under $N_2$ was placed 5.4 grams para-formaldehyde, 66 mL methanol and 0.96 grams 50 weight percent aqueous NaOH (0.012 moles). This was heated to reflux and a solution of 30.9 grams (0.15 moles) of 2,6-di-tert-butylphenol in 15 mL methanol was added over a two hours period at reflux. The reaction mixture was then transferred under $N_2$ to a pressure reaction vessel. The vessel was sealed and heated at 95° C. for 2.5 hours with stirring. The mixture was neutralized with HCl. The solvent and volatiles were evaporated. The residue was dissolved in ether, washed twice with water and dried over $MgSo_4$. The ether was evaporated and the residue (35 grams) analyzed by gas chromatography. (See Table I)

TABLE I

| Catalyst | Ether[1] | Bis-phenol[2] | Phenol[3] | Formal[4] | Un-known |
|---|---|---|---|---|---|
| Sodium hydroxide | 30.2% | 44.8% | 0% | 0% | 21.8% |
| Dimethylamine | 91.7% | 3.2% | 0.3% | 2.0% | 1.4% |

[1] 2,6-di-tert-butyl-4-methoxymethylphenol
[2] 4,4'-methylenebis(2,6-di-tert-butylphenol)
[3] 2,6-di-tert-butylphenol
[4] 2,6-di-tert-butyl-4-methoxymethoxymethylphenol It was observed that in Example 3 using sodium hydroxide the amount of ether product at the end of the addition of 2,6-di-tert-butylphenol was 56% but continued reaction with unreacted 2,6-di-tert-butylphenol consumed ether product forming large amounts of bisphenol by-product.

The results show that by following the process of the present invention an intermediate ether can be made in over 90% yield with very low bisphenol formation. Prior art procedures using alkali metal hydroxides give much lower yields and form large amounts of bisphenol by-product.

The above examples demonstrate formation of the catalyst in situ but of course the catalyst could be separately added.

I claim:

1. A process for the production of aromatic ethers of structure

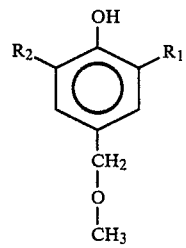

comprising reacting at a temperature of 50°–200° C. in the presence of a Mannich base catalyst: formaldehyde; a stoichiometric excess of methanol and a substituted phenol of structure

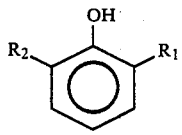

wherein $R_1$ and $R_2$ are the same or different and are lower alkyl groups.

2. The process of claim 1 carried out at a pressure of about 5–100 psig.

3. The process of claim 1 wherein said Mannich base is of the structure

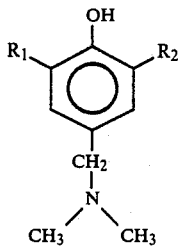

wherein $R_1$ and $R_2$ are the same or different and are lower alkyl groups.

4. The process of claim 3 wherein said formaldehyde is paraformaldehyde.

5. The process of claim 4 wherein said Mannich base is formed in situ from a portion of said substituted phenol, paraformaldehyde and a catalyst-forming portion of dimethylamine.

6. The process of claim 5 wherein said temperature is 60°–130° C.

7. The process of claim 1 wherein said formaldehyde is paraformaldehyde.

8. The process of claim 7 wherein said temperature is 60°–130° C.

9. The process of claim 8 wherein $R_1$ and $R_2$ are alkyl of 1 to 6 carbon atoms.

10. The process of claim 9 wherein $R_1$ and $R_2$ are tert-butyl.

11. The process of claim 7 wherein said temperature is 60°–130° C.

12. A process for the production of 2,6-di-tert-butyl-4-methoxymethylphenol, said process comprising reacting at a temperature of about 60°–130° C. in the presence of a Mannich base catalyst: paraformaldehyde, a stoichiometric excess of methanol and 2,6-di-tert-butylphenol.

13. A process of claim 12 wherein said Mannich base is formed in situ by reacting a small catalyst-forming amount of dimethylamine with said paraformaldehyde and 2,6-di-tert-butylphenol.

14. A process for the production of 1,3,5-trimethyl-2,4,6-tris(3,5-di-tert-butyl-4-hydroxybenzyl)benzene with conversation of catalyst materials, elimination of centrifugation of a chemical intermediate, and minimization of by-product bisphenol intermediate, said process comprising the steps of;

(a) reacting at a temperature of about 60°–130° C. 2,6-di-tert-butylphenol, paraformaldehyde, and a stoichiometric excess of methanol in the presence of a catalytic portion of 2,6-di-tert-butyl-4-dialkylaminomethylphenol so as to form the intermediate 2,6-di-tert-butyl-α-methoxy-p-cresol, said catalytic portion being formed from a dialkyl secondary amine, whereby some of the secondary amine remains in the unreacted excess methanol and formation of 4,4'-methylenebis(2,6-di-tert-butylphenol) is minimized;

(b) distilling the unreacted excess methanol containing some of the secondary amine and reycling said methanol to another intermediate formation reaction thereby conserving catalyst;

(c) dissolving the intermediate 2,6-di-tert-butyl-α-methoxy-p-cresol in methylene chloride thereby eliminating the need for centrifugation;

(d) reacting the dissolved intermediate with mesitylene in the presence of a sulfuric acid or Friedel-Crafts catalyst; and (e) recovering the 1,3,5-trimethyl-2,4,6-tris(3,5,-di-tert-butyl-4-hydroxybenzyl)benzene product.

15. The process of claim 14 wherein said dialkyl secondary amine in step (a) is dimethylamine.

16. The proces of claim 15 wherein said catalyst in step (d) is sulfuric acid.

17. The process of claim 16 wherein said reaction in step (d) is carried out at about −10° to 30° C.

18. A process for the production of aromatic ethers of the structure

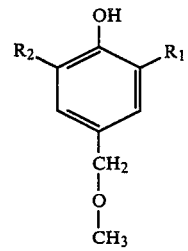

comprising reacting at a temperature of 50–200° C. a mixture of a substituted phenol of structure

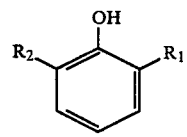

wherein $R_1$ and $R_2$ are the same or different and are lower alkyl groups, with formaldehyde, a stoichiometric excess of methanol and a small amount of a dialkylamine.

19. A process of claim 18 for making 2,6-di-tert-butyl-4-methoxymethylphenol wherein said substituted phenol is 2,6-di-tert-butylphenol, said dialkylamine is dimethylamine and said small amount is 0.01–0.1 moles per mole of said 2,6-di-tert-butylphenol.

* * * * *

UNITED STATES PATENT AND TRADEMARK OFFICE
CERTIFICATE OF CORRECTION

PATENT NO. : 4,754,077

DATED : JUNE 28, 1988

INVENTOR(S) : George L. Mina

It is certified that error appears in the above-identified patent and that said Letters Patent is hereby corrected as shown below:

Column 1, line 32 reads "1,3,5-trimethly-" and should read -- 1,3,5-trimethyl- -- .

Column 1, line 33 reads "hydroxybenzl)benzene" and should read -- hydroxybenzyl)benzene -- .

Column 1, line 34 reads "3,5-dialkyl-4-hydroxybenzly" and should read -- 3,5-dialkyl-4-hydroxybenzyl -- .

Column 2, line 65 reads "same of" and should read -- same or -- .

Column 3, line 14 reads "hydocarbon" and should read -- hydrocarbon -- .

Column 5, line 6 reads "2,6di-lower" and should read -- 2,6-di-lower -- .

Column 5, line 6 reads "2,6di-cycloalkyphenols" and should read -- 2,6-di-cycloalkylphenols -- .

UNITED STATES PATENT AND TRADEMARK OFFICE
CERTIFICATE OF CORRECTION

PATENT NO. : 4,754,077

DATED : JUNE 28, 1988

INVENTOR(S) : George L. Mina

It is certified that error appears in the above-identified patent and that said Letters Patent is hereby corrected as shown below:

Column 5, line 10 reads "2,6-dicyclopentyphenol" and should read -- 2,6-dicyclopentylphenol -- .

Column 5, line 18 reads "2,6diisopropylphenol" and should read -- 2,6-diisopropylphenol -- .

Column 5, line 24 reads "butyl-α methoxy" and should read -- butyl-α-methoxy -- .

Column 5, line 25 reads "butyl-α- ethoxy" and should read -- butyl-α-ethoxy -- .

Column 5, line 26 reads "butyl-3-5,-dimethyl" and should read -- butyl-3,5-dimethyl --.

Column 5, line 30 reads "dicyclohexyl-αmethoxy" and should read -- dicyclohexyl-α-methoxy -- .

UNITED STATES PATENT AND TRADEMARK OFFICE
CERTIFICATE OF CORRECTION

PATENT NO. : 4,754,077

DATED : JUNE 28, 1988

INVENTOR(S) : George L. Mina

It is certified that error appears in the above-identified patent and that said Letters Patent is hereby corrected as shown below:

Column 5, line 49 reads "which tey" and should read -- which they -- .

Column 5, line 60 reads "methylaminoprop1)" and should read -- methylaminopropyl -- .

Column 5, line 63 reads "are most" and should read -- are more -- .

Column 5, line 66 reads "use amy" and should read -- use may -- .

Column 6, line 9 reads "especailly" and should read -- especially -- .

Column 7, line 10 reads "dimethlamine" and should read -- dimethylamine -- .

Column 8, line 6 reads "presuure" and should read -- pressure -- .

UNITED STATES PATENT AND TRADEMARK OFFICE
CERTIFICATE OF CORRECTION

PATENT NO. : 4,754,077

DATED : JUNE 28, 1988

INVENTOR(S) : George L. Mina

It is certified that error appears in the above-identified patent and that said Letters Patent is hereby corrected as shown below:

Column 8, line 17 reads "obviates such" and should read -- obviates the need for severe mechanical separation of the intermediate such -- .

Column 8, line 66 reads "nittogen" and should read -- nitrogen -- .

Column 11, line 61 reads "conversation" and should read -- conservation -- .

Column 12, line 15 reads "reycling" and should read -- recycling -- .

Signed and Sealed this

Eighteenth Day of October, 1988

Attest:

DONALD J. QUIGG

Attesting Officer

Commissioner of Patents and Trademarks